United States Patent
Haddon

(12) 
(10) Patent No.: US 6,428,912 B1
(45) Date of Patent: Aug. 6, 2002

(54) ELECTRON TRANSPORT MATERIAL AND LIGHT EMITTING DIODE THAT CONTAINS THE ELECTRON TRANSPORT MATERIAL

(75) Inventor: Robert C. Haddon, Lexington, KY (US)

(73) Assignee: Agere Systems Guardian Corp., Orlando, FL (US)

( * ) Notice: Subject to any disclaimer, the term of this patent is extended or adjusted under 35 U.S.C. 154(b) by 0 days.

(21) Appl. No.: 09/164,161

(22) Filed: Sep. 30, 1998

(51) Int. Cl.[7] .................. H05B 33/12; C07C 49/788; C07C 225/22; C07C 251/02
(52) U.S. Cl. .................. 428/690; 428/917; 313/504; 313/506; 552/286; 552/290; 556/175; 568/326
(58) Field of Search .................. 428/690, 917, 428/704; 313/504, 506; 552/286, 290; 556/170, 176, 181, 182, 175; 568/326

(56) References Cited

U.S. PATENT DOCUMENTS

| | | | |
|---|---|---|---|
| 3,180,730 A | | 4/1965 | Klupfel |
| 3,530,325 A | | 9/1970 | Mehl et al. |
| 3,567,450 A | | 3/1971 | Brantly et al. |
| 3,658,520 A | | 4/1972 | Brantly et al. |
| 4,175,960 A | | 11/1979 | Berwick et al. .............. 430/58 |
| 4,356,429 A | | 10/1982 | Tang ........................ 313/503 |
| 4,440,693 A | * | 4/1984 | Naarmann et al. |
| 4,539,507 A | | 9/1985 | VanSlyke et al. .......... 313/504 |
| 5,061,569 A | | 10/1991 | VanSlyke et al. .......... 428/457 |
| 5,095,099 A | * | 3/1992 | Parkinson et al. .......... 534/15 |
| 5,294,870 A | * | 3/1994 | Tang et al. ................ 313/504 |
| 5,552,547 A | * | 9/1996 | Shi ............................ 546/7 |

OTHER PUBLICATIONS

Yi–Zhen Hu et al., "Studies on the chelation of hypocrellin A with aluminium ion . . . complex", J. Photochem. Photobiol. B: Biol. 22, pp. 219–227, 1994 (no month).*

Yoichi Demura et al., "Metal Chelates of 9–hydroxy–1–phenalenone", Bull. Chem. Soc. Jpn. 48(10), pp. 2820–2824, 1975 (no month).*

* cited by examiner

Primary Examiner—Marie Yamnitzky
(74) Attorney, Agent, or Firm—King and Schickli PLLC

(57) ABSTRACT

An improved multilayer light emitting device includes novel compounds for use as the electron transporting layer. In particular, the novel compounds are novel aluminum cheltates (e.g. tris(9-oxidophenalenone) aluminum [Al(9-opo)$_3$] and tris(6-oxidobenzanthrone) aluminum [Al(6-obao)$_3$]. These compounds are electron acceptors having improved thermal stability while in most cases and in most applications maintaining comparable efficiencies. When negatively biased, electrons are infected into the electron transporting layer. The concurrent positive bias on the anode in relation to the cathode causes holes to be injected from the cathode into the hole transporting layer. Electroluminescence is produced and confined generally near the interface between these electron and hole transporting layers an a result of the recombination of the electron and hole pairs.

10 Claims, 1 Drawing Sheet

ELECTRON TRANSPORT MATERIAL AND LIGHT EMITTING DIODE THAT CONTAINS THE ELECTRON TRANSPORT MATERIAL

TECHNICAL FIELD

The present invention relates generally to light emitting devices that contain organic electron transport materials and more particularly to novel organic compounds for use as electron transport materials.

BACKGROUND OF THE INVENTION

Early light emitting or electroluminescent devices utilized only a single layer of organic luminescent material sandwiched between two injecting electrodes. The first electrode injected holes and the second electrode injected electrons into the organic material. As described in U.S. Pat. No. 3,530,325 to Mehl et al., one such device utilized a single crystal anthracene as the organic material. The most significant disadvantage to the use of anthracene, however, is the unacceptably high drive voltage required to produce a significant or commercially viable amount of light. In fact, the required drive voltage was determined to be 100 volts or higher. Necessarily, the power-consumption efficiency of these early devices was quite low and typically less than 0.1% W/W.

The primary factor contributing to the high drive voltage was the inability to reduce the thickness of the anthracene layer below 50 μm. Attempts to reduce the thickness of these and related materials in order to reduce the drive voltage, proved overall to be unsuccessful. Although some success was achieved in reducing the drive voltage below 30 volts, the reduction of the anthracene layer to 1 μm or less resulted in the formation of pinholes which acted as shorts between the electrodes. These shorts virtually eliminated the amount of luminescence produced. Even the addition of non-conductive polymeric binders as a remedy for the pinholes proved generally unsuccessful due to the interference of the binders with the injection of holes and electrons. As a result, and despite lowering the required drive voltage, these devices offered only very low quantum efficiencies of about 0.05%.

More recently, double-layered light emitting devices manufactured using organic thin films have been developed. These devices typically include a cathode of a low-work-function metal or alloy for efficient electron injection, an anode of indium-tin-oxide, an aromatic diamine for the hole injecting or transporting layer and a luminescent film of aluminum tris(8-oxy-1-quinoline) ($Alq_3$) from a class of fluorescent metal chelate complexes for the electron injecting or transporting layer. This particular double-layered device has proven to be successful in lowering the required drive voltage (approximately 6–14 volts) while maintaining sufficient quantum efficiencies of about 1.0%. Despite these advances, concern regarding the commercialization of these devices still remains and revolves primarily around their overall stability during continuous operation.

In particular, it is known that these particular double-layered light emitting devices incur a relatively fast degradation of the electroluminescence emission. More specifically, tests have shown an initial degradation of around 30% over the first ten hour period to about 50% over a one hundred hour period. Thus, a need is identified for improved organic compounds for use in these multilayered devices having a low drive voltage, high quantum efficiency and which overcome the present problem of relatively rapid degradation of the electroluminescence emission.

SUMMARY OF THE INVENTION

An important aspect of the present invention is to provide electron transport materials for use in light emitting devices that contain the electron transport material having a low drive voltage, improved thermal stability while in most cases and in most applications maintaining comparable efficiencies. In particular, the improved thermal stability, comparable efficiency and high yields are due to the utilization of novel electron transport materials for transporting electrons in the light emitting device.

Thus, in accordance with the preferred embodiment of our present invention, the light emitting device includes an electron transporting material formed as a layer in contact with a hole transporting material similarly formed as a layer. These layers are further confined between two electrodes. A power source is connected in a conventional manner to each of the electrodes. The first electrode, or cathode, is electrically connected to the electron transporting layer and the second electrode, or anode, is likewise connected to the hole transporting layer. When the cathode is negatively biased in relation to the anode, electrons are injected into the electron transporting layer. The concurrent positive bias on the anode in relation to the cathode causes holes to be injected from the cathode into the hole transporting layer. Electroluminescence is produced and confined generally near the interface between the electron and hole transporting layers as a result of the recombination of the electron and hole pairs.

In accordance with an important aspect of the present invention, the electron transporting layer is an aluminum chelate prepared from various polycyclic aromatic compounds selected from a group including hydroxyphenalenones, hydroxybenzanthrones, phenalenes, hydroxybenzanthracenones and mixtures thereof including particularly phenalenone and/or a benzanthrone based precursors including, for example, the following compounds:

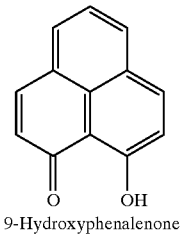

9-Hydroxyphenalenone (1)

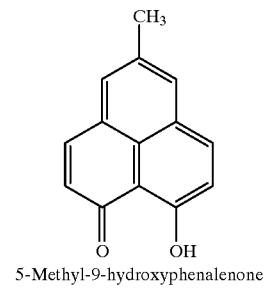

5-Methyl-9-hydroxyphenalenone (2)

-continued (3)

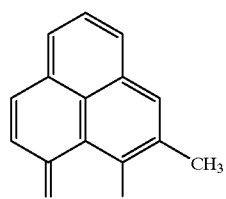
2-Methyl-9-hydroxyphenalenone (4)

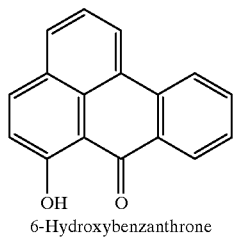
6-Hydroxybenzanthrone (5)

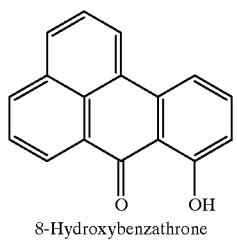
8-Hydroxybenzanthrone (6)

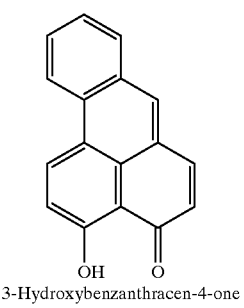
3-Hydroxybenzanthracen-4-one (7)

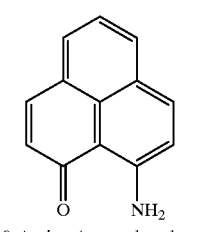
9-Amino-1-oxo-phenalene (8)

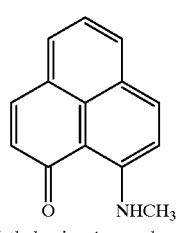
9-Methylamino-1-oxo-phenalene

-continued (9)

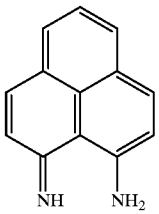
9-Amino-1-phenalene (10)

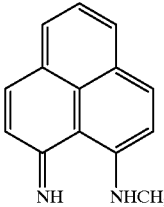
9-Methylamino-1-imino-phenalene (11)

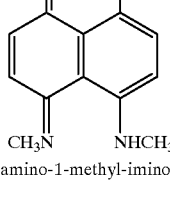
9-Methylamino-1-methyl-imino-phenalene

9-Methylamino-1-methyl-imino-phenalene

In the most preferred embodiments, the electron transporting layer is formed from tris-(9-oxidophenalenone) aluminum [Al(9-opo)$_3$] and/or a benzannellated derivative thereof, tris (6-oxidobenzanthrone) aluminum [Al(6-obao)$_3$], compounds 1 and 4 respectively. These compounds are electron acceptors having improved thermal stability while in most cases and in most applications maintaining comparable efficiencies.

BRIEF DESCRIPTION OF THE DRAWINGS

The accompanying drawing incorporated in and forming apart of the specification, illustrates several aspects of the present invention and together with the description serves to explain the principles of the invention. In the drawings.

Reference will now be made in detail to the present preferred embodiment of the invention, an example of which is illustrated in the accompanying drawings.

DETAILED DESCRIPTION OF THE PREFERRED INVENTION

Figure 1:
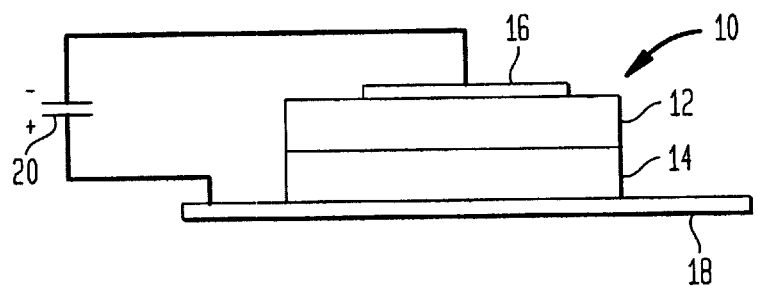
FIG. 1 is a partial schematic plan view of the light emitting device of the present invention.

Reference is now made to the partial schematic view of FIG. 1 showing an improved light emitting device 10 of the invention. In the preferred embodiment of the present invention, the light emitting device 10 includes an electron transporting layer 12 in direct contact with a hole transporting layer 14. The electron and hole transporting layers 12, 14 are positioned between and in direct contact with two electrodes 16, 18. The first electrode, or cathode 16, is in direct contact with the electron transporting layer 12 and the second electrode, or anode 18, is in direct contact with the hole transporting layer 14. Each cathode may be formed from various metals such as aluminum, silver, magnesium, calcium, lithium and alloys thereof. Each of the electron and hole transporting layers 12, 14 as well as the electrodes 16, 18 in the present preferred embodiment are deposited by vacuum deposition on a transparent substrate (not shown). Such a substrate may be made from, for example, a thin layer of indium tin oxide (ITO) on glass in accordance with procedures well known to those skilled in the art. Alternate methods for depositing the various layers/electrodes known in the art may also be used during fabrication.

Efficient injection of holes and electrons is provided from an indium-tin-oxide anode 18 and an electropositive metal or alloy cathode 16, such as aluminum or magnesium. It is well known in the art, however, that additional similar electrically conductive transparent oxides or other light transmissive layers of any of the high work function metals are sufficient to provide efficient hole injection. Further, numerous low-work-function alloys such as Mg:Al are also sufficient to provide efficient electron injection and may even lower the required drive voltage.

During operation, a power source 20 is connected in a conventional manner to each of the electrodes 16, 18 described above. When the cathode 16 is negatively biased in relation to the anode 18, electrons are injected from the anode into the electron transporting layer 12. The concurrent positive bias on the anode 18 in relation to the cathode 16 causes holes to be injected from the cathode into the hole transporting layer 14. Accordingly, electroluminescence is produced and confined generally near the interface between the electron and hole transporting layers 12, 14 as a result of the recombination of the electron and hole pairs.

In the present preferred embodiment, the hole transporting layer 14 is formed from an aromatic amine including, particularly, tertiary amines such as described in U.S. Pat. No. 5,294,870 to Tang et al. Useful aromatic tertiary amines include unsubstituted and substituted arylamines such as monoarylamine, diarylamine, triarylamine or polymeric arylamine. Examples of these and other appropriately substituted arylamines may be found in, for example, U.S. Pat. No. 3,180,730 to Klupfel and U.S. Pat. Nos. 3,567,450 and 3,658,520 both to Brantley et al.

In addition, unsubstituted and substituted tetraaryldiamines may also be utilized as the hole transporting layer 14. Preferred tetraaryldiamines include two diarylamino groups. Typical substituents in the substituted compounds identified above include but are not limited to alkyl groups, alkoxy groups, aryl groups, aryloxy groups and halogens such as fluoride, chloride and bromide. Additional examples for appropriate compounds for the hole transporting layer 14 are found in, for example, U.S. Pat. No. 4,175,960 to Berwick et al. and U.S. Pat. Nos. 4,539,507 and 5,061,569 both to Van Slyke et al.

The electron transporting layer 12 in the present preferred embodiment is formed from an aluminum chelate preferably prepared from a polycyclic aromatic compound selected from a group including hydroxyphenalenones, hydroxybenzanthrones, phenalenes, hydroxybenzanthracenones and mixtures thereof including particularly phenalenones and/or a benzanthrone-based precursors including but not limited to the following compounds:

(1)

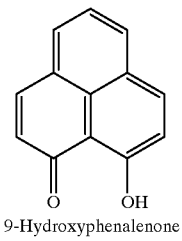

9-Hydroxyphenalenone (2)

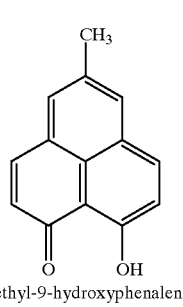

5-Methyl-9-hydroxyphenalenone (3)

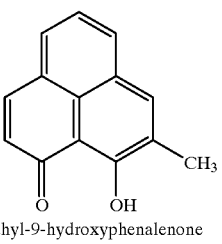

2-Methyl-9-hydroxyphenalenone (4)

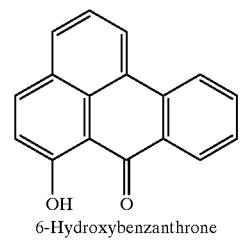

6-Hydroxybenzanthrone (5)

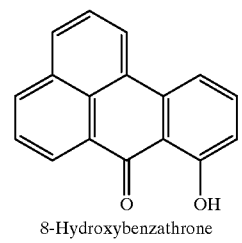

8-Hydroxybenzathrone

-continued (6)
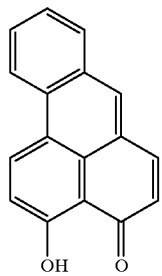
3-Hydroxybenzanthracen-4-one (7)
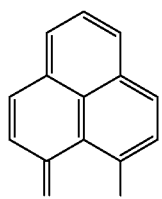
9-Amino-1-oxo-phenalene (8)
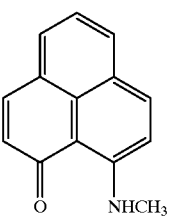
9-Methylamino-1-oxo-phenalene (9)
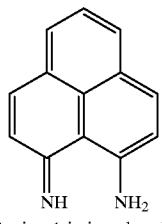
9-Amino-1-imino-phenalene

(10)
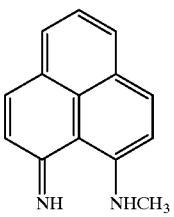
9-Methylamino-1-imino-phenalene

(11)
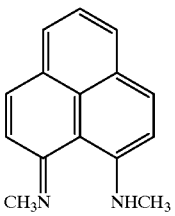
9-Methylamino-1-methyl-imino-phenalene

The aluminum chelate is preferably prepared by mixing, refluxing and reacting one of the above precursor compounds with aluminum chloride in the presence of a suitable solvent such as dry toluene. The resulting aluminum chelates have the following structural formulae:

(12)
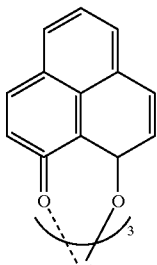
Tris-(9-oxidophenalenone) aluminum

(13)
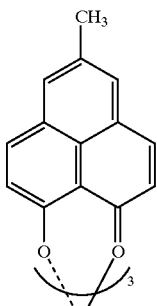
Tris (5-methyl-9-oxidophenalenone) aluminum

(14)
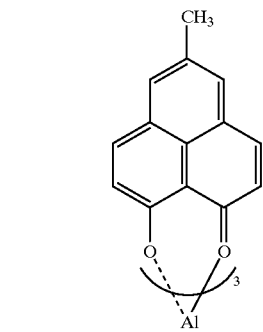
Tris (2-methyl-9-oxidophenalenone) aluminum

(15)
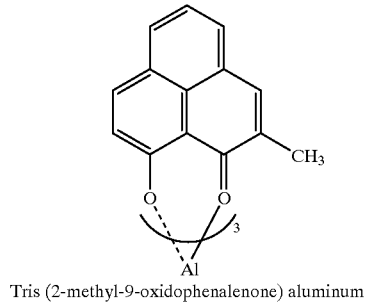
Tris (6-oxidobenzanthrone) aluminum (16)

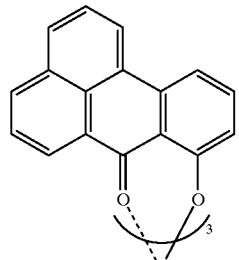

Tris (8-oxidobenzanthrone) aluminum (17)

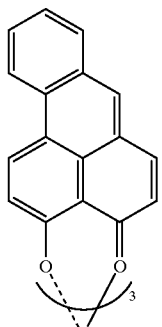

Tris (3-oxidobenzanthracen-4-one) aluminum (18)

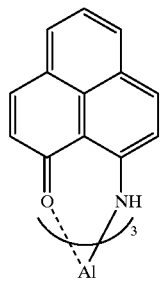

Tris (9-imino-1-oxo-phenalene) aluminum (19)

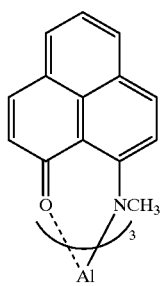

Tris (9-methylimino-1-oxo-phenalene) aluminum (20)

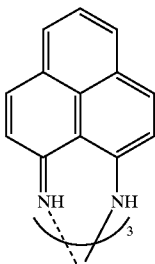

Tris (9-inimo-1-oxo-phenalene) aluminum (21)

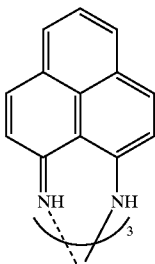

Tris (9-methylimino-1-imino-phenalene) aluminum (22)

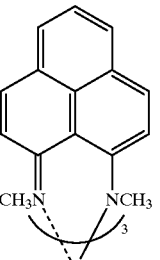

Tris (9-methylimino-1-methylimino-Phenalene) aluminum

It is advantageous if the electron transporting layer 12 is formed from tris (9-oxidophenalenone) aluminum [Al(9-opo)$_3$] or tris (6-oxidobenzanthrone) aluminum [Al(6-obao)$_3$] (see formulae 12 and 15 respectively). The electrochemistry of these aluminum chelate compounds reveals that they are an electron acceptor and have excellent thermal stability. This is demonstrated by the fact that tris (9-oxidophenalenone) aluminum [Al(9-opo)$_3$] has a reduction potential of E½=−0.3V and a decomposition temperature of 440° C., whereas the prior art compound aluminum tris (8-oxido-1-quinoline)(Alq$_3$) has a reduction potential of E½=−1.53 V and a decomposition temperature of 412° C. The following examples are provided for the manufacture of the various aluminum chelates useful as the electron transporting layer 12.

Figure 2:
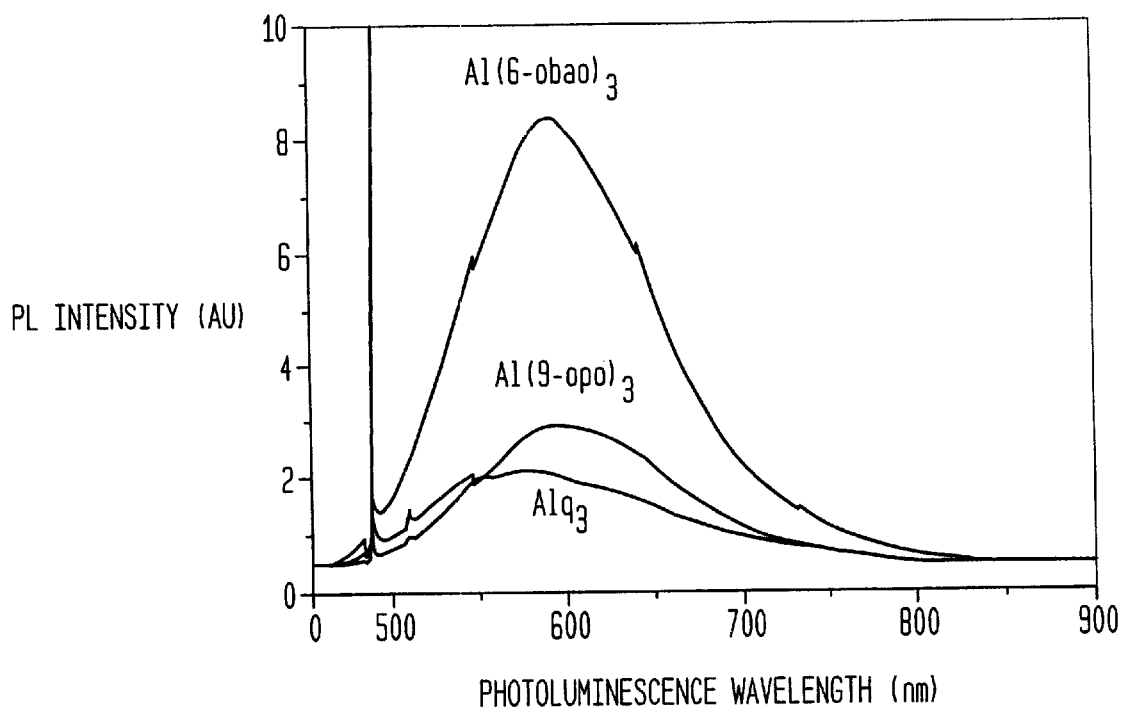
FIG. 2 is a graphical illustration demonstrating the relative luminescence yields which is a good measure of efficiency of the two most preferred electron transporting layers of the present invention (Al(6-obao)$_3$ and Al(9-opo)$_3$) and the known prior art electron transporting layer of aluminum tris (8-oxy-1-quinoline) (Alq$_3$).

The photoluminescence yields of representative materials are given in FIG. 2. It is understood that photoluminescence yield is a useful measure of efficiency of emitter materials. At the frequency of irradiation (excitation at approximately 400 nm) as shown in FIG. 2, these preferred materials exhibit a high degree of efficiency. Measurements of the relative efficiencies of $Alq_3$ and $Al(6\text{-}obao)_3$ as the electron transporting/emitting layer in comparable LEDs shows that $Alq_3$ is more efficient than $Al(6\text{-}obao)_3$ by a factor of about two. The reversal between photoluminescence and electroluminescence yields is presumably an indication that the photoluminescence of these compounds is not uniform across the spectral range of the emission.

EXAMPLE 1

Preparation of Tris (9-oxidophenalenone) aluminum [Al(9-opo)$_3$]

9-Hydroxyphenalenone (1.5 g) was placed in a 100 mL round-bottom flask. Dry toluene (50 mL) was added to the flask together with aluminum chloride (0.113 g). The solution turned yellow-orange, and a precipitate began to form. The mixture was refluxed at 110° C. overnight. The flask was then cooled and the contents filtered. Crude yield 1.69 g, mp>300° C.

The crude product was first purified by recrystallization from anisole/methanol and then subjected to fractional sublimation. The desired compound $C_{39}H_{21}O_6Al$ sublimes as a yellow film at about 340° C., under a vacuum of $4\times10^{-5}$ torr.

EXAMPLE 2

Preparation of Tris (6-oxidobenzanthrone) aluminum [Al(6-oboa)$_3$]

6-Hydroxy benzanthrone (1.0 g) was placed in a 100 mL round-bottom flask. Dry toluene (50 mL) was added to the flask together with aluminum chloride (0.113 g). The solution turned yellow-orange, and a precipitate began to form. The mixture was refluxed at 110° C. overnight. The flask was then cooled and the contents filtered. Crude yield 0.62 g, mp>300° C.

The crude product was first purified by recrystallization from anisole/methanol (0.38 g) and then subjected to fractional sublimation. The desired compound $C_{51}H_{27}O_6Al$ sublimes as a yellow film at about 340° C. under a vacuum of $4\times10^{-5}$ torr.

EXAMPLE 3

5-Methyl-9-hydroxyphenalenone (1.5 g) is placed in 100 ml round-bottom flask. Dry toluene (50 mL) is added to the flask together with aluminum chloride (0.113 g). The solution turns yellow-orange and a precipitate begins to form. The mixture is then refluxed at 110° C. overnight. The flask is then cooled and the contents are filtered. After purification by recrystallization from anisole/methanol and fractional sublimation the desired compound $C_{42}H_{27}O_6Al$ sublimes as a yellow film at about 340° C. under a vacuum of $4\times10^{-5}$ torr.

EXAMPLE 4

2-Methyl-9-hydroxphenalenone (1.5 g) is placed in 100 ml round-bottom flask. Dry toluene (50 mL) is added to the flask together with aluminum chloride (0.113 g). The solution turns yellow-orange and apreciptate begins to form. The mixture is then refluxed at 110° C. overnight. The flask is then cooled and the contents are filtered. After purification by recrystallization from anisole/methanol and fractional sublimation the desired compound $C_{42}H_{27}O_6Al$ sublimes as a yellow film at about 340° C. under a vacuum of $4\times10^{-5}$ torr.

EXAMPLE 5

8-Hydroxybenzanthrone (1.0 g) is placed in 100 ml round-bottom flask. Dry toluene (50 mL) is added to the flask together with aluminum chloride (0.113 g). The solution turns yellow-orange and a precipitate begins to form. The mixture is then refluxed at 110° C. overnight. The flask is then cooled and the contents are filtered. After purification by recrystallization from anisole/methanol and fractional sublimation the desired compound $C_{51}H_{27}O_6Al$ sublimes as a yellow film at about 340° C. under a vacuum of $4\times10^{-5}$ torr.

EXAMPLE 6

3-Hydroxybenzanthracen-4-one is placed in 100 ml round-bottom flask. Dry toluene (50 mL) is added to the flask together with aluminum chloride (0.113 g). The solution turns yellow-orange and a precipitate begins to form. The mixture is then refluxed at 110° C. overnight. The flask is then cooled and the contents are filtered. After purification by recrystallization from anisole/methanol and fractional sublimation the desired compound $C_{51}H_{27}O_6Al$ sublimes as a yellow film at about 340° C. under a vacuum of $4\times10^{-5}$ torr.

EXAMPLE 7

9-Amino-1-oxo-phenalene (1.5 g) is placed in 100 ml round-bottom flask. Dry toluene (50 mL) is added to the flask together with aluminum chloride (0.113 g). The solution turns yellow-orange and a precipitate begins to form. The mixture is then refluxed at 110° C. overnight. The flask is then cooled and the contents are filtered. After purification by recrystallization from anisole/methanol and fractional sublimation the desired compound $C_{39}H_{24}O_3N_3Al$ sublimes as a yellow film at about 340° C. under a vacuum of $4\times10^{-5}$ torr.

EXAMPLE 8

9-Methylamino-1-oxo-phenalene (1.5 g) is placed in 100 ml round-bottom flask. Dry toluene (50 mL) is added to the flask together with aluminum chloride (0.113 ). The solution turns yellow-orange and a precipitate begins to form. The mixture is then refluxed at 110° C. overnight. The flask is then cooled and the contents are filtered. After purification by recrystallization from anisole/methanol and fractional sublimation the desired compound $C_{42}H_{30}O_6N_3Al$ sublimes as a yellow film at about 340° C. under a vacuum of $4\times10^{-5}$ torr.

EXAMPLE 9

9-Amino-1-imino-phenalene (1.5 g) is placed in 100 ml round-bottom flask. Dry toluene (50 mL) is added to the flask together with aluminum chloride (0.113 g). The solution turns yellow-orange and a precipitate begins to form. The mixture is then refluxed at 110° C. overnight. The flask is then cooled and the contents are filtered. After purification by recrystallization from anisole/methanol and fractional sublimation the desired compound $C_{39}H_{27}N_6Al$ sublimes as a yellow film at about 340° C. under a vacuum of $4\times10^{-5}$ torr.

EXAMPLE 10

9-Methylamino-1-imino-phenalene (1.5 g) is placed in 100 ml round-bottom flask. Dry toluene (50 mL) is added to the flask together with aluminum chloride (0.113 g). The solution turns yellow-orange and aprecipitate begins to form. The mixture is then refluxed at 110° C. overnight. The flask is then cooled and the contents are filtered. After purification by recrystallization from anisole/methanol and fractional sublimation the desired compound $C_{42}H_{33}N_6Al$ sublimes as a yellow film at about 340° C. under a vacuum of $4\times10^{-5}$ torr.

EXAMPLE 11

5-Methyl-9-hydroxyphenalenone (1.5 g) is placed in 100 ml round-bottom flask. Dry toluene (50 mL) is added to the flask together with aluminum chloride (0.113 g). The solution turns yellow-orange and aprecipitate begins to form. The mixture is then refluxed at 110° C. overnight. The flask is then cooled and the contents are filtered. After purification by recrystallization from anisole/methanol and fractional sublimation the desired compound $C_{45}H_{39}N_6Al$ sublimes as a yellow film at about 340° C. under a vacuum of $4\times10^{-5}$ torr.

EXAMPLE 12

A light emitting device is prepared by vacuum deposition on an indium tin oxide (ITO) coated glass substrate. Specifically, the glass substrate is mounted on a stage facing a series of tantalum boats mounted on a turret containing the various organic components (diarylamine hole transporter and the aluminum chelate electron transporter/emitter to be tested) and metals for electrode formation in a bell jar that is then evacuated to a pressured of about $10^{-6}$ torr. The organic layers or films are deposited sequentially from the individual tantalum boats by resistive heating.

The deposition is monitored with a quartz crystal microbalance, and the rate is controlled to be about 50 A°/minute. The hole and electron transporting layers are typically deposited to a thickness of about 500 A°. The metal electrodes (aluminum, silver, magnesium, calcium, lithium or alloys thereof), are then formed directly on top of the organic layers by evaporation. These depositions are carried out without breaking the vacuum by use of shadow masks that are sequentially rotated in front of the substrate. Testing is carried out in situ using a proprietary procedure. Thus fabrication and efficiency may be directly determined and compared in situ without exposing the devices to the atmosphere.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best application to thereby enable one of ordinary skill in the art to utilize the invention in various embodiments and with various modifications as are suited to the particular use contemplated. All such modifications and variations are within the scope of he invention as determined by the appended claims when interpreted in accordance with the breadth to which they are fairly, legally and equitably entitled.

What is claimed is:

1. A light emitting device for producing light when connected to a power source, comprising:
    an anode;
    a cathode;
    a hole transporting layer having a first face and a second face, said first face being in contact with said anode; and
    an electron transporting layer having a third face being in contact with said cathode and a fourth face being in contact with said second face of said hole transporting layer;
    said electron transporting layer being formed from an aluminum chelate derived from a compound selected from the group consisting of:

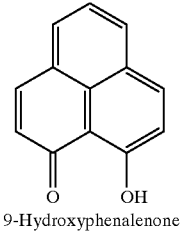

9-Hydroxyphenalenone (1)

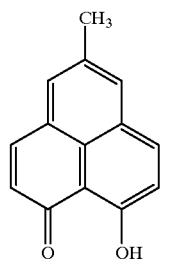

5-Methyl-9-hydroxyphenalenone (2)

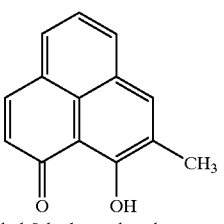

2-Methyl-9-hydroxyphenalenone (3)

6-Hydroxybenzanthrone (4)

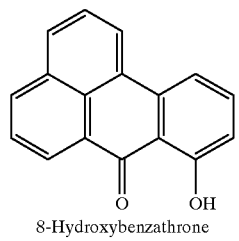

8-Hydroxybenzathrone (5)

-continued

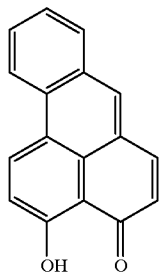
3-Hydroxybenzanthracen-4-one

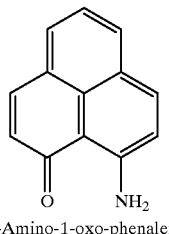
9-Amino-1-oxo-phenalene

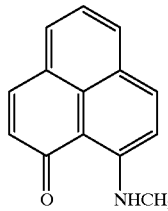
9-Methylamino-1-oxo-phenalene

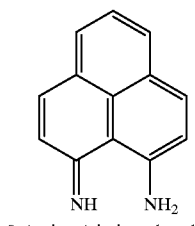
9-Amino-1-imino-phenalene

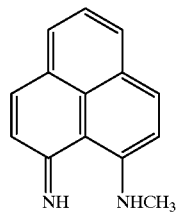
9-Methylamino-1-imino-phenalene

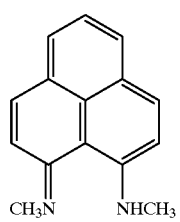
9-Methylamino-1-methyl-imino-phenalene

2. The light emitting device for producing light of claim 1, wherein said cathode is comprised of a low-work-function alloy.

3. The light emitting device for producing light of claim 1, wherein said anode is comprised of indium tin oxide.

4. The light emitting device for producing light of claim 1, wherein said hole transporting layer is comprised of an aromatic amine.

5. The light emitting device for producing light of claim 1, wherein said electron transporting layer is comprised of Tris(9-oxidophenalenone) aluminum.

6. The light emitting device for producing light of claim 1, wherein said electron transporting layer is comprised of Tris (6-oxidobenzanthrone) aluminum.

7. A light emitting device for producing light when connected to a power source, comprising:

an anode;

a cathode;

a hole transporting layer having a first face and a second face, said first face being in contact with said anode; and an electron transporting layer having a third face being in contact with said cathode and a fourth face being in contact with said second face of said hole transporting layer;

said electron transporting layer being formed from an aluminum chelate derived from a hydroxybenzanthracenone.

8. A aluminum chelate derived from a compound selected from the group consisting of:

(1)

6-Hydroxybenzanthrone (2)

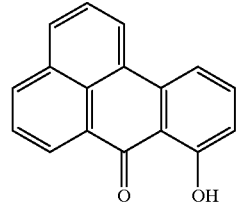
8-Hydroxybenzanthrone (3)

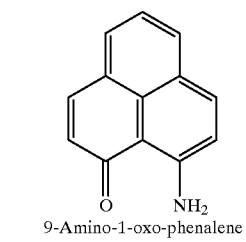
9-Amino-1-oxo-phenalene (4)

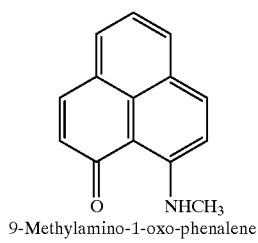
9-Methylamino-1-oxo-phenalene (5)

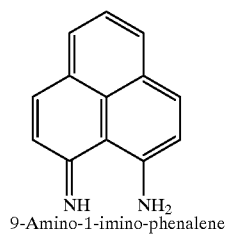
9-Amino-1-imino-phenalene (6)

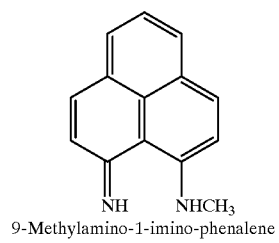
9-Methylamino-1-imino-phenalene (7)

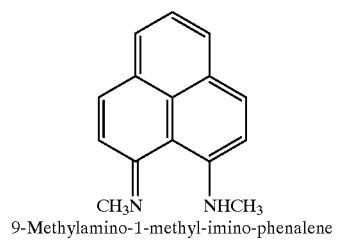
9-Methylamino-1-methyl-imino-phenalene

9. An aluminum chelate selected from the group consisting of:

(2)

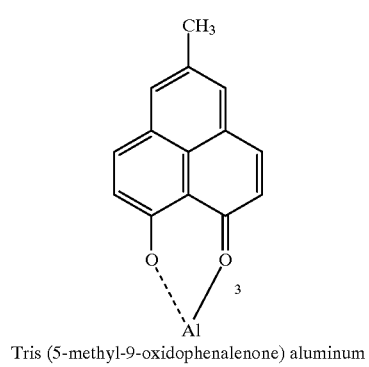
Tris (5-methyl-9-oxidophenalenone) aluminum (3)

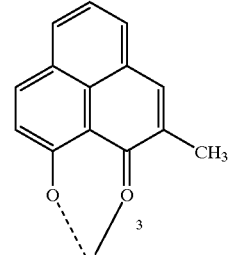
Tris (2-methyl-9-oxidophenalenone) aluminum (4)

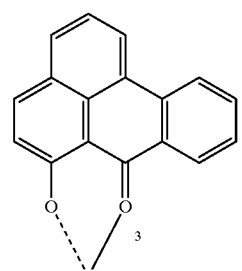
Tris (6-oxidobenzanthrone) aluminum (5)

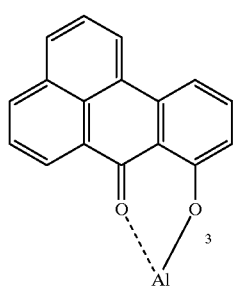
Tris (8-oxidobenzanthrone) aluminum (6)

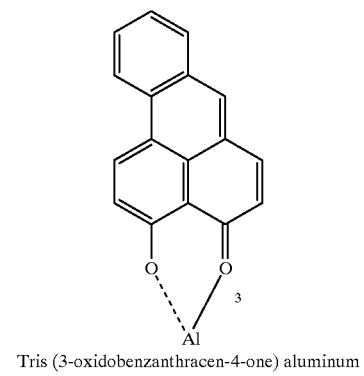
Tris (3-oxidobenzanthracen-4-one) aluminum

-continued (7)

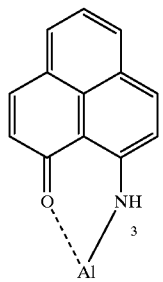

Tris (9-imino-1-oxo-phenalene) aluminum (8)

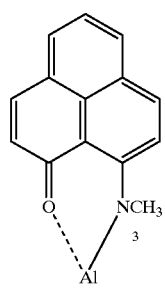

Tris (9-methylimino-1-oxo-phenalene) aluminum (9)

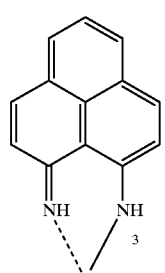

Tris (9-imino-1-oxo-phenalene) aluminum (10)

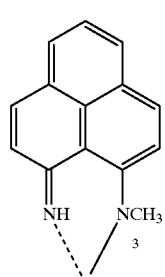

Tris (9-methylimino-1-imino-phenalene) aluminum (11)

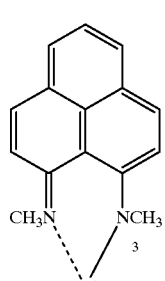

Tris (9-methylimino-1-methylimino-phenalene) aluminum.

10. A light emitting device for producing light when connected to a power source, comprising:

an anode;

a cathode;

a hole transporting layer having a first face and a second face, said first face being in contact with said anode; and an electron transporting layer having a third face being in contact with said cathode and said fourth face being in contact with said second face of said hole transporting layer;

said electron transporting layer being formed from an aluminum chelate selected from the group consisting of:

(1)

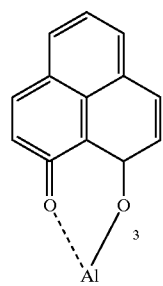

Tris-(9-oxidophenalenone) aluminum (2)

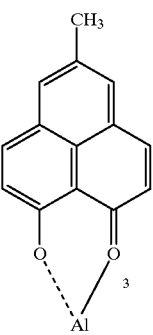

Tris (5-methyl-9-oxidophenalenone) aluminum (3)

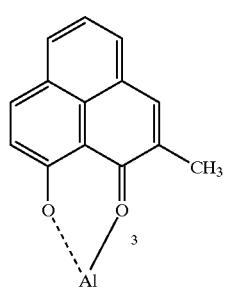

Tris (2-methyl-9-oxidophenalenone) aluminum

-continued
(4)
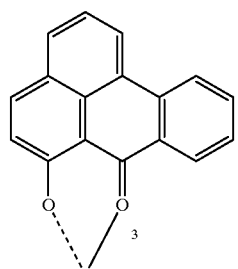
Tris (6-oxidobenzanthrone) aluminum
(5)
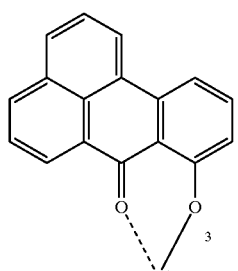
Tris (8-oxidobenzanthrone) aluminum
(6)
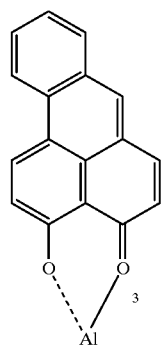
Tris (3-oxidobenzanthracen-4-one) aluminum
(7)
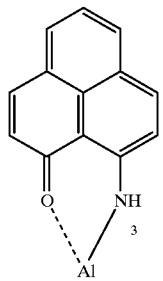
Tris (9-imino-1-oxo-phenalene) aluminum
-continued
(8)
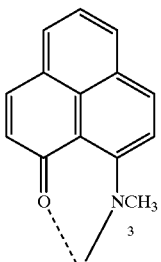
Tris (9-methylimino-1-oxo-phenalene) aluminum
(9)
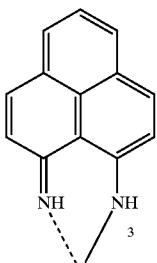
Tris (9-imino-1-oxo-phenalene) aluminum
(10)
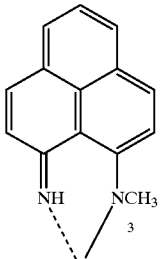
Tris (9-methylimino-1-imino-phenalene) aluminum
(11)
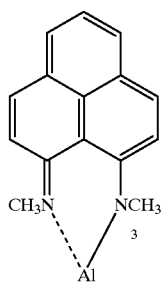
Tris (9-methylimino-1-methylimino-phenalene) aluminum.
* * * * *